United States Patent
Faubert et al.

(10) Patent No.: US 6,416,481 B2
(45) Date of Patent: Jul. 9, 2002

(54) FLICKER-INDUCED INTEROCULAR TRANSFER-OF-OXYGENATION FOR NON-INVASIVELY ASSESSING NEURAL INTEGRITY OF A PATIENT'S CENTRAL NERVOUS SYSTEM

(75) Inventors: Jocelyn Faubert, Notre-Dame-de-l'Ile-Perrot; Vasile Diaconu, L'Ile-Perrot, both of (CA)

(73) Assignee: Universite de Montreal, Montreal (CA)

( * ) Notice: Subject to any disclaimer, the term of this patent is extended or adjusted under 35 U.S.C. 154(b) by 0 days.

(21) Appl. No.: 09/844,619

(22) Filed: Apr. 27, 2001

Related U.S. Application Data
(60) Provisional application No. 60/200,384, filed on Apr. 28, 2000.

(51) Int. Cl.[7] ................................................. A61B 5/00
(52) U.S. Cl. ....................................................... 600/558
(58) Field of Search ................................ 600/544, 546, 600/558, 323, 355, 356

(56) References Cited

U.S. PATENT DOCUMENTS

| | | | | |
|---|---|---|---|---|
| 5,308,919 A | * | 5/1994 | Minnich | 128/633 |
| 6,149,589 A | * | 11/2000 | Diaconu et al. | 600/318 |
| 6,312,393 B1 | * | 11/2001 | Abreu | 600/558 |

FOREIGN PATENT DOCUMENTS

WO  WO 99/48418  9/1999

OTHER PUBLICATIONS

Thomas et al., "Amplitude Response and Stimulus Presentation Frequency Response of Human Primary Visual Cortex Using BOLD EPI at 4T", *MRM*, Williams & Wilkins, vol. 40, 1998, pp. 203–209.

Ahmed et al., "The Oxygen Distribution in the Prelaminar Optic Nerve Head of the Cat", *Exp. Eye Res.*, Academic Press Limited, vol. 59, 1994, pp. 458–465.

Andrews et al., "Temporal Events in Cyclopean Vision", *Proc. Natl. Acad. Sci. USA*, vol. 93, Apr. 1996, pp. 3689–3692.

Staedt et al., "Einfluß einer Hämodilution mit 10%iger Hydroxyäthylstärkelösung rkelosung (MW 200000/0,5) auf die Fließeigenschaften des Blutes, die arteriellen Blutgase und den konjunktivalen Sauerstoffpartialdruck bei Patienten mit Hirninfarkt", *Infusionstherapie*, vol. 16, Mar. 1989, pp. 107–112 *.

Dahlem et al., "Does the migraine aura reflect cortical organization?", *European Journal of Neuroscience*, European Neuroscience Association, vol. 12, 2000, pp. 767–770.

Donnet et al., "Migraine with Visual Aura and Photosensitive Epileptic Seizures", *Epilepsia*, Lippincott–Raven Publishers, vol. 38 No. 9, 1997, pp. 1032–1034.

Kager et al., "Simulated Seizures and Spreading Depression in a Neuron Model Incorporating Interstitial Space and Ion Concentrations", *Journal of Neurophysiology*, The American Physiological Society, vol. 84, No. 1, Jul. 2000, pp. 495–512.

(List continued on next page.)

*Primary Examiner*—Max Hindenburg
(74) *Attorney, Agent, or Firm*—Fay Kaplun & Marcin LL

(57) ABSTRACT

In the method and apparatus for assessing neural integrity of a patient's central nervous system, the patient is stimulated with a visual or auditory flickering stimulus, and oxygenation in the patient's second eye is sensed. Finally, the method and apparatus detects whether a change in the sensed oxygenation occurs in response to stimulation of the patient with the visual or auditory flickering stimulus. This change in the sensed oxygenation is indicative of neural integrity of the patient's central nervous system.

18 Claims, 4 Drawing Sheets

OTHER PUBLICATIONS

Kaube et al., "Aura in Some Patients with Familial Hemiplegic Migraine Can be Stopped by Intranasal Ketamine", *Nuerology* 2000, AAN Enterprises, Inc., vol. 55, No. 1, 2000, pp. 139–141.

Pantoni et al., "Transient Global Amnesia: A review Emphasizing Pathogenic Aspects", *Acta Neurol Scand* 2000, Munksgaard 2000, vol. 102, 2000, pp. 275–283.

Sotak C. H., "New NMR Measurements in Epilepsy Diffusion–Weighted Magnetic Resonance Imaging of spreading Depression", *Jasper's Basic Mechanisms of the Epilepsies Third Edition: Advances in Neurology*, Lippincott Williams & Wilkins, vol. 79, Chapter 63: New NMR Measurements in Epilepsy, Section V: Frontiers in Brain Imaging and Therapeutics, 1999, pp. 925–929.

Faubert et al., "The O.S.O.M.E. SYSTEM: A New Real–Time Non–Invasive Technique for Measuring Oxygenation and Hemoglobin in the Human Eye", Ocular Blood Flow II Paper Presentations, 5145–12:15, *IOVS*, vol. 40, No. 4, Mar. 15, 1999.

* cited by examiner

US 6,416,481 B2

FLICKER-INDUCED INTEROCULAR TRANSFER-OF-OXYGENATION FOR NON-INVASIVELY ASSESSING NEURAL INTEGRITY OF A PATIENT'S CENTRAL NERVOUS SYSTEM

This application claims benefit of 60/200,384 filed Apr. 28, 2000.

BACKGROUND OF THE INVENTION

1. Field of the Invention

The present invention relates to a method and apparatus for assessing the neural integrity of a patient's central nervous system.

2. Brief Description of the Prior Art

It is well known to those of ordinary skill in the art that'stimulating an eye with flickering light induces strong neural activity resulting in oxygen consumption of the human brain [Thomas, C. G.; Menon, R. S.; (1998); "Amplitude Response and Stimulus Presentation Frequency Response of Human Primary Visual Cortex Using BOLD EPI at 4 T"; *Magnetic Resonance Medicine*, 40, 203–209] and the optic nerve head of the cat [Ahmed J.; Linsenmeier, R. A.; Dunn, R. Jr.; (1994); "The Oxygen Distribution in the Prelaminar Optic Nerve Head of the Cat"; *Experimental Eye Research*, 59, 457–465]. It is also known from the literature that selective adaptation or stimulation of one eye will induce sensitivity changes in the other, contralateral eye; this phenomenon is called "interocular transfer" [Andrews T. J.; White, L. E.; Binder, D,;Purves, D.; (1996); "Temporal Events in Cyclopean Vision"; *Proceedings of the National Academy of Sciences USA*, 93, 3689–3692]. These studies imply the role of central mechanisms, e.g. the human brain, as being responsible for the control of the sensitivity changes observed in the contralateral eye. It is also reported that cerebral infarcts will induce oxygen changes measured at the level of the contralateral eye [Staedt, U.; Hutt M.; Herrmann B.; Seufzer, U.; Leweling H.; (1989); "Effect of Hemoglobin with 10% Hydroxyethyl Starch Solution (MW 200,000/9.5) on the Flow Properties of Blood, Arterial Blood Gases and Conjunctival Oxygen Partial Pressure in Patients with Cerebral Infarct"; *Infusionstherapie*, 16, 107–112].

Epilepsy, migraines with visual auras, and temporary amnesia have all been associated with cortical depression spreading (CD) in the brain, as reported in the following articles:

[Dahlem, M. A.; Engelmann, R.; Lowel, S.; Muller, S. C.; (2000); "Does the Migraine Aura Reflect Cortical Organization?; *Eur J Neurosci*, 12, 767–770];

[Donnet A.; Bartolomei, F.; (1997); "Migraine with Visual Aura and Photosensitive Epileptic Seizures"; *Epilepsia*, 38, 1032–1034];

[Kager, H.; Wadman, W. J.; Somjen, G. G.; (2000); "Simulated Seizures and Spreading Depression in a Neuron Model Incorporating Interstitial Space and Ion Concentration"; *J Neurophysiol.*, 84, 495–512];

[Kaube, H.; Herzog, J.; Kaufer, T.; Dichgans, M.; Diener, H. C.; (2000); "Aura in Some Patients with Familial Hemiplegic Migraine can be Stopped by Intranasal Ketamine"; *Neurology*, 55, 139–141];

[Pantoni, L.; Lamassa, M.; Inzitari, D.; (2000); "Transient Global Amnesia; A Review Emphasizing Pathogenic Aspects"; *Acta Neurol Scand.*, 102, 275–283]; and

[Sotak, C. H.; (1999); "New NMR Measurements in Epilepsy. Diffusion-Weighted Magnetic Resonance Imaging of Spreading Depression"; *Adv Neurol*, 79, 925–929].

Cortical depression spreading can be induced by stimulation and results in a widespread decrease in oxygenation of the brain followed by a change in neural potentials.

OBJECTS OF THE INVENTION

An object of the present invention is to assess the neural integrity of the central nervous system of a patient by stimulating the patient with a visual or auditory flickering stimulus and detecting oxygenation changes in at least one eye of the patient.

SUMMARY OF THE INVENTION

More specifically, in accordance with the present invention, there is provided a method for assessing neural integrity of a patient's central nervous system, comprising stimulating the patient with a visual or auditory flickering stimulus, sensing oxygenation in at least one eye of the patient, and detecting whether a change in the sensed oxygenation occurs in response to stimulation of the patient with the flickering stimulus. This change is indicative of neural integrity of the patient's central nervous system.

Also in accordance with the present invention, there is provided an apparatus for assessing neural integrity of a patient's central nervous system, comprising a generator of a visual or auditory flickering stimulus, and a neural integrity assessment instrument responsive to oxygenation in at least one eye of the patient. The flickering stimulus is applied to the patient to stimulate this patient, and the neural integrity assessment instrument comprises:

a sensor of oxygenation in at least one eye of the patient; and a detector of a change in the level of the sensed oxygenation in response to stimulation of said patient with the flickering stimulus, this change being indicative of neural integrity of the patient's central nervous system.

The present invention further relates to method for assessing neural integrity of a patient's central nervous system, comprising stimulating a first eye of the patient with a flickering light, sensing oxygenation in the patient's second eye, and detecting whether a change in the sensed oxygenation occurs in response to stimulation of the patient's first eye with flickering light, this change being indicative of neural integrity of the patient's central nervous system.

In accordance with preferred embodiments of this method:

sensing oxygenation in the patient's second eye comprises sensing levels of oxygenation at the optic nerve head of the fundus of the patient's second eye; and stimulating the patient's first eye comprises adjusting at least one of the following parameters to generate at least one desired neural response of the patient's central nervous system: an intensity of the flickering light, a contrast of the flickering light, a color of the flickering light, a flicker rate of the flickering light, and a duration of the stimulation of the patient's first eye with flickering light.

The present invention still further relates to an apparatus for assessing neural integrity of a patient's central nervous system, comprising a generator of flickering light applied to a first eye of the patient to stimulate this patient's first eye, and a neural integrity assessment instrument responsive to oxygenation in the patient's second eye. The neural integrity assessment instrument comprising:

a sensor of oxygenation in the patient's second eye; and a detector of a change in the level of the sensed oxygenation in response to stimulation of the patient's first eye with flickering light, this change being indicative of neural integrity of the patient's central nervous system.

According to preferred embodiments of this apparatus:

the sensor is positioned to sense levels of oxygenation at the optic nerve head of the fundus of the patient's second eye;

the generator comprises a source of light operated through a flickering-light controller, the source of light is selected from the group consisting of a light-emitting diode and a laser, and a fiber optic cable is interposed between the source of light and the patient's first eye to guide light from the source of light to the patient's first eye; and the neural integrity assessment instrument comprises an on-line oxygenation measurement device.

Still further in accordance with the present invention, there is provided a method for assessing neural integrity of a patient's central nervous system, comprising stimulating at least one ear of the patient with an auditory flickering stimulus, sensing oxygenation in at least one eye of the patient, and detecting whether a change in the sensed oxygenation occurs in response to stimulation of the patient's at least one ear with the auditory flickering stimulus, this change being indicative of neural integrity of the patient's central nervous system.

According to a preferred embodiment, stimulating the patient's at least one ear comprises adjusting at least one of the following parameters to generate at least one desired neural response of the patient's central nervous system: an amplitude of the auditory flickering stimulus, a frequency of the auditory flickering stimulus, a pitch domain of the auditory flickering stimulus, a flicker rate of the auditory flickering stimulus, and a duration of the stimulation of the patient's at least one ear with the auditory flickering stimulus.

Again in accordance with the present invention, there is provided an apparatus for assessing neural integrity of a patient's central nervous system, comprising:

a generator of an auditory flickering stimulus, this auditory flickering stimulus being applied to at least one ear of the patient to stimulate this patient's at least one ear;

a neural integrity assessment instrument responsive to oxygenation in at least one eye of the patient, this neural integrity assessment instrument comprising:

a sensor of oxygenation in the patient's at least one eye; and a detector of a change in the level of the sensed oxygenation in response to stimulation of the patient's at least one ear with the auditory flickering stimulus, this change being indicative of neural integrity of the patient's central nervous system.

According to a preferred embodiment of this apparatus, the generator comprises a source of auditory flickering stimulus connected to an earphone.

The foregoing and other objects, advantages and features of the present invention will become more apparent upon reading of the following non restrictive description of preferred embodiments thereof, given for the purpose of illustration only with reference to the accompanying drawings.

DETAILED DESCRIPTION OF THE PREFERRED EMBODIMENTS

At present, nobody has tested or proposed an apparatus for stimulating a first eye of a patient with flickering light and for measuring and detecting the effect of flicker-induced changes on the oxygen level of the second, contralateral eye of the same patient. Such an apparatus would have a great impact on assessing the integrity, in particular but not exclusively, of the human central nervous system (brain) as a consequence of cerebrovascular accidents, brain infarcts, brain traumas, epilepsy, migraines, or any other neuro-pathological condition produced by accidents (e.g. internal hemorrhaging), diseases, drugs, or toxins.

Such an apparatus would also have a great impact on measuring the widespread decrease in oxygenation of the brain (central nervous system) followed by a change in neural potentials, which results from cortical depression spreading; this would enable determination of whether patients are at risk and whether given medications are efficient in avoiding CD.

Such an apparatus would also have a great impact for evaluating treatment drugs for any neurological disorder such as anticonvulsive drugs for the treatment of epilepsy, migraine medication, neuro-protective agents, psychotropic medication, etc. Furthermore, testing the neural integrity with such a device could indicate the level of alertness for patients under anesthesia.

Figure 1:
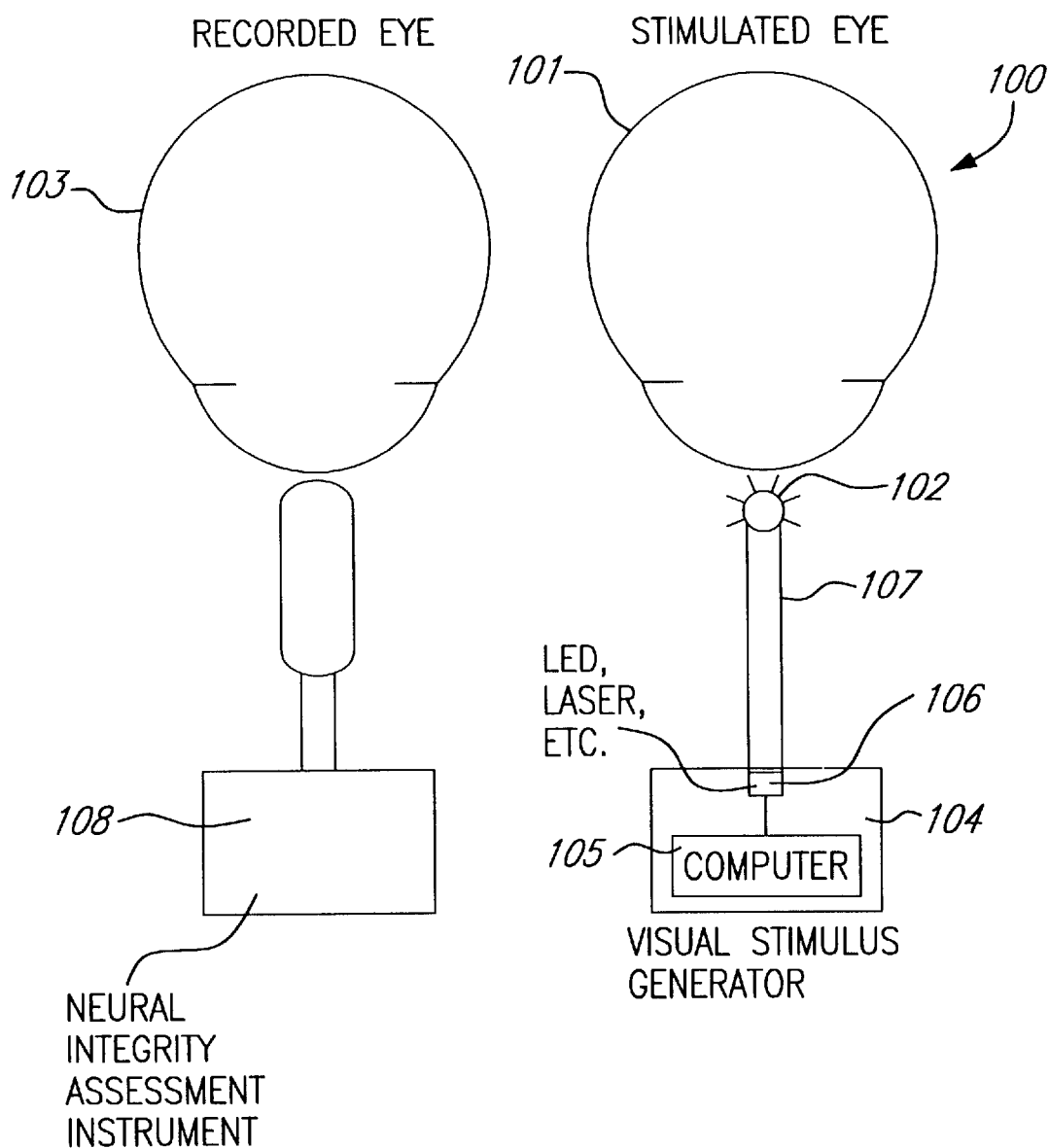
FIG. 1 is a schematic block diagram of an apparatus according to the present invention, for assessing neural integrity of a patient's central nervous system by means of a visual stimulus.

Visual Flickering Stimulus:

A first preferred embodiment of the present invention, as illustrated in FIG. 1, comprises an apparatus 100 for assessing neural integrity of a patient's central nervous system. This apparatus 100 stimulates a first eye 101 of the patient with flickering light 102 and senses oxygenation levels in the second, contralateral eye 103 of the same patient. Preferably, but not exclusively, these levels of oxygenation are sensed at the optic nerve head of the fundus of the eye. Of course, it is within the scope of the present invention to measure oxygenation levels at any other suitable locations in or on the second, contralateral eye 103.

Referring to FIG. 1, the apparatus 100 comprises a visual stimulus generator 104. This stimulus generator 104 essentially consists of a flickering-light controller, which can be a computer such as 105 coupled with a light-emitting diode (LED) (see 106), a laser (see 106), or any other suitable source of light (see 106). The flickering light 102 can be guided from the light'source 106 to the stimulated eye 101 via a fiber optic cable 107. Alternatively, the LED, laser or any other source of light 106 can be placed directly in the proximity of the stimulated eye 101.

The intensity, contrast, color, and flicker rate of the light 102, as well as the duration of the test (duration of the stimulation of the eye 101 with flickering light) could all be adjusted to generate a desired neural response or different neural responses of the patient's central nervous system. Of course, it is important to adjust the above parameters to levels susceptible to cause no damage to the patient's eye 101.

Still referring to FIG. 1, the apparatus 100 further comprises a neural integrity assessment instrument 108. In the preferred embodiment, the neural integrity assessment instrument 108 comprises the device for on-line and real-time spectroreflectometry measurement of oxygenation in a patient's eye as described in International patent application WO 99/48418 (Faubert et al.) published on Sep. 30, 1999. The subject matter of this International patent application WO 99/48418 is incorporated herein by reference. However, it'should be kept in mind that it is within the scope of the present invention to use any other suitable type of neural integrity assessment device 108.

Figure 2:
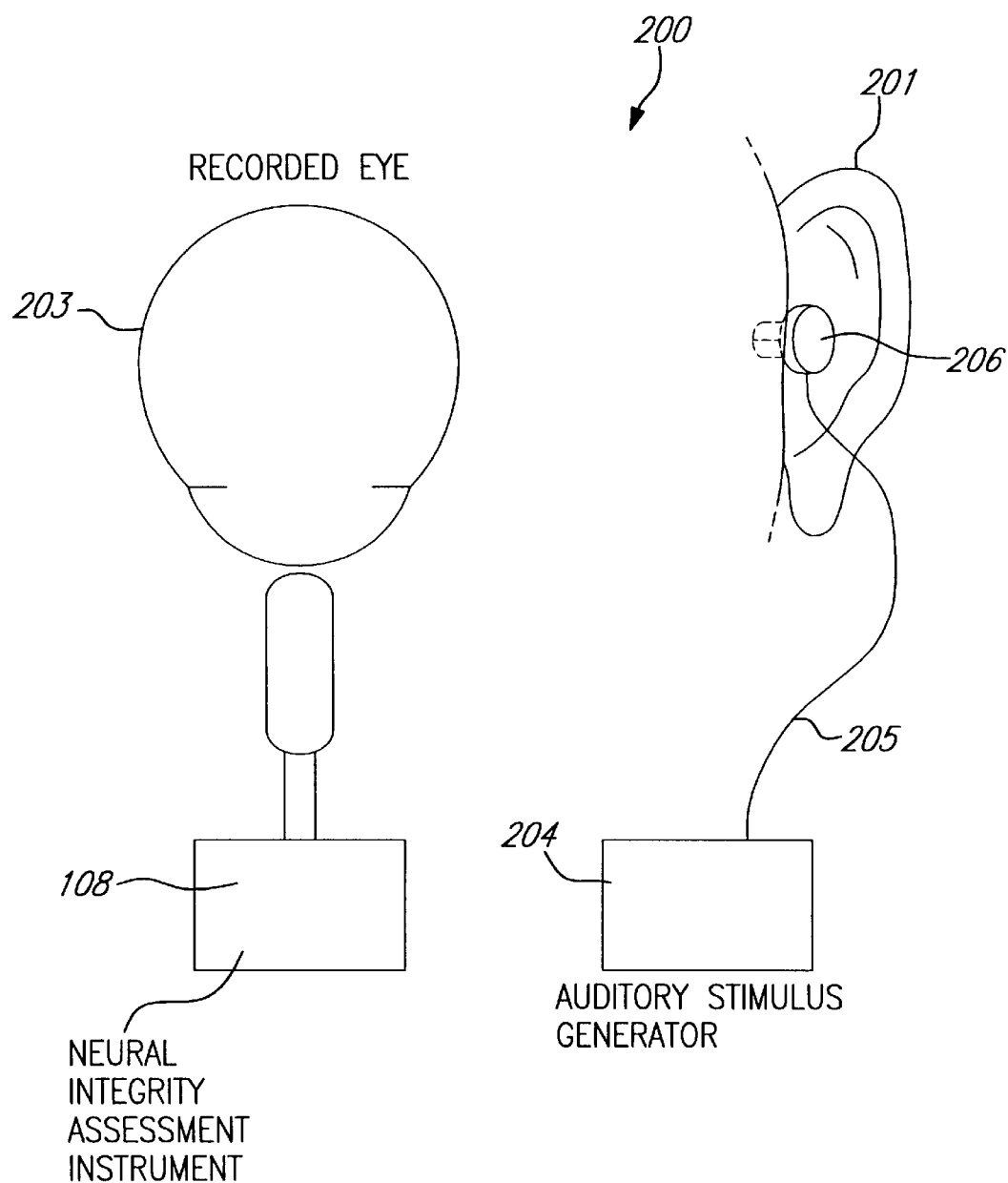
FIG. 2 is a schematic block diagram of an apparatus according to the present invention, for assessing neural integrity of a patient's central nervous system by means of an auditory stimulus.

Auditory Flickering Stimulus:

A second preferred embodiment of the present invention, as illustrated in FIG. 2, comprises an apparatus 200 for assessing neural integrity of a patient's central nervous system. This apparatus 200 stimulates at least one ear 201 of the patient with an auditory flickering stimulus and senses oxygenation levels in at least one eye 203 of the same patient. Preferably, but not exclusively, these levels of oxygenation are sensed at the optic nerve head of the fundus of the eye. Of course, it is within the scope of the present invention to measure oxygenation levels at any other suitable locations in or on the eye 203.

Referring to FIG. 2, the apparatus 100 comprises an auditory stimulus generator 204. This stimulus generator 104 essentially consists of a computer generating the auditory flickering stimulus applied to the patient's ear 201 through an electric wire 205 and an earphone 206. Normally, the auditory flickering stimulus will consists of an audible sound.

The amplitude, frequency, pitch domain and flicker rate of the auditory flickering stimulus, as well as the duration of the test (duration of the stimulation of the ear 201 with the auditory flickering stimulus) could all be adjusted to generate a desired neural response or different neural responses of the patient's central nervous system. Of course, it is important to adjust the above parameters to levels susceptible to cause no damage to the patient's ear 201.

Still referring to FIG. 2, the apparatus 100 further comprises a neural integrity assessment instrument 108. In the second preferred embodiment, the neural integrity assessment instrument 108 again comprises the device for on-line and real-time spectroreflectometry measurement of oxygenation in a patient's eye as described in International patent application WO 99/48418 (Faubert et al.) published on Sep. 30, 1999. The subject matter of this International patent application WO 99/48418 is incorporated herein by reference. However, it'should be kept in mind that it is within the scope of the present invention to use any other suitable type of neural integrity assessment device 108.

Figure 3:
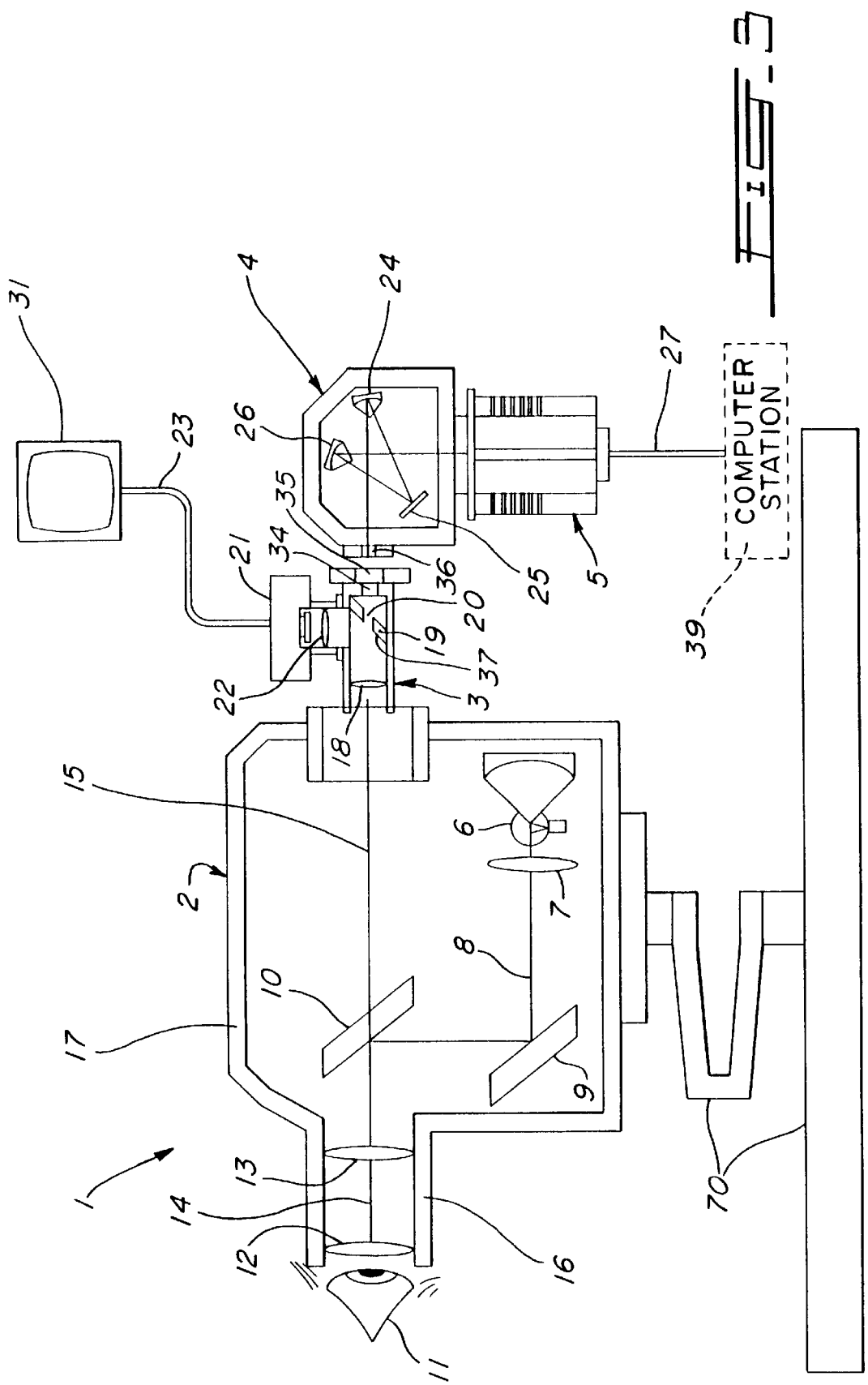
FIG. 3 is a schematic diagram of a spectroreflectometry oxygenation measurement device used in the apparatuses of FIGS. 1 and 2, for assessing neural integrity of a patient's central nervous system.

Neural Integrity Assessment Instrument:

A device as described in International patent application WO 99/48418, for on-line and real-time spectroreflectometry measurement of oxygenation in a patient's eye is illustrated in FIG. 3 and generally identified by the reference 1. This device 1 comprises a fundus camera 2, a camera-to-spectrograph interface 3, and a detector unit formed of a spectrograph 4 and a CCD (Charge Coupled Device) detector array 5.

Sensor of the Neural Integrity Assessment Instrument:

The fundus camera 2 is supported by a mechanical frame 70 schematically illustrated in FIG. 3.

Still referring to FIG. 3, the fundus camera 2 comprises a light'source 6 for producing light having a predetermined relatively wide spectral (frequency) bandwidth optimized for spectroreflectometry oxygenation measurement. In this respect, the spectroreflectometry oxygenation measurement of hemoglobin and its derivatives such as oxyhemoglobin and carbonylhemoglobin is preferably conducted within a spectral bandwidth including the range of wavelengths comprised between 450 nm and 850 nm.

Light is propagated from a light'source 6 to a region of the fundus of the patient's eye 11 by a first optical system. As indicated in the foregoing description, oxygenation sensing is preferably made at the optic nerve head of the fundus of the eye. This first optical system comprises:

a lens 7 to concentrate light generated by the source 6 into a light beam 8;

45° mirror 9 and 45° beam splitter 10 to reflect the light beam 8 twice and transmit that light beam 8 to the patient's eye 11 along a linear trajectory 14; and a pair of lenses 12 and 13 mounted along the trajectory 14 to propagate the light beam 8 toward the desired region of the fundus of the patient's eye 11.

The intensity of the light beam 8 must be sufficiently low for being applied to the fundus of the patient's eye for the duration of the test without harming the patient's eye. Preferably, the light beam 8 will have an intensity lower than 5 mW/cm$^2$, which is safe for exposure time as long as 6 minutes.

As can be seen in FIG. 3, the fundus camera 2 is formed with a housing 17 defining a cylindrical portion 16 in which the pair of lenses 12 and 13 are mounted. The cylindrical portion 16 defines with the lens 12 the objective of the fundus camera 2. Obviously, the patient places his (or her) eye 11 close to and in front of the lens 12 of the fundus camera 2.

Light beam 8 is reflected at least in part by the fundus of the patient's eye 11 to produce a reflected light beam 15 having a geometrical longitudinal axis (not shown). A second optical system propagates the reflected light beam along a predetermined propagation path 14 from the fundus of the patient's eye 11 to the detector (4, 5, 39).

The second optical system comprises the pair of lenses 12 and 13, and the 45° beam splitter 10 to propagate the reflected light beam 15 from the fundus of the patient's eye 11 along the propagation path 14 toward the camera-to-spectrograph interface 3. 45° beam splitter 10 will cause no reflection of the reflected light beam 15 propagating along path 14 from the fundus of the patient's eye 11 to the interface 3.

The second optical system also comprises a lens 18 and a 45° mirror 19 of the camera-to-spectrograph interface 3. More specifically, the lens 18 propagates the reflected light beam 15 along the propagation path 14 toward the 45° mirror 19. Mirror 19 defines an angle of 45° and comprises a central, axial opening 20 having a predetermined diameter centered on the geometrical longitudinal axis of the reflected light beam 15. Of course, the central axial opening 20 will transmit to the detector (4, 5, 39) only the axial central portion of the reflected light beam 15. The second optical system further comprises axial apertures such as 34, 35 and 36 provided in the housings of the camera-to-interface 3 and spectrograph 4 to enable the axial central portion of the reflected light beam 15 to reach the spectrograph 4.

Just a word to mention that the use of the axial central portion of the reflected 37 lightbeam 15 enables selection of a small precise area which is optimal for oxygenation sensing of specific structures such as the blindspot, arteries, veins, etc.

The mirror 19 comprises a light-reflecting annular surface 37 surrounding the axial central opening 20. The reflected light beam 15 comprises an axial peripheral portion surrounding the axial central portion and reflected by the light-reflecting annular surface 37 of the mirror. The axial peripheral portion of the reflected light beam 15 is deviated by 90° by reflection on the light-reflecting annular surface 37 of the 45° mirror 19 to propagate toward a TV camera 21 through a lens 22 of the camera-to-spectrograph interface 3.

The image sensed by the TV camera 21 is displayed on a TV monitor 31 through a cable 23. This enables the operator to visualize the fundus of the patient's eye and the location of the axial central opening 20 on the fundus of the patient's eye, and therefore to select the small central area of interest where spectroreflectometry oxygenation sensing is desired.

Detector of the Neural Integrity Assessment Instrument:

The spectrograph 4 comprises a first concave mirror 24 having a generally elliptical cross section to receive the axial central portion of the reflected light beam 15 and to deflect this axial central light beam portion toward a generally planar diffraction grating 25. Diffraction grating 25 consists of an array of narrow slits or grooves which produce a large number of beams interfering with each other to produce a light spectrum. As it is well known to those of ordinary skill in the art, this light spectrum includes light components of the axial central portion of the reflected light beam 15 arranged in order of wavelength. The produced light spectrum is reflected by a second concave mirror 26 also having a generally elliptical cross section and deviated toward the CCD detector array 5.

In other words, the diffraction grating 25 separates the light components of different wavelengths within the range comprised between 450 nm and 850 nm. The intensities of the light components of different wavelengths of the light spectrum are detected and measured by the CCD detector array 5. For example, the CCD detector array 5 consists of a two-dimensional array comprising 1024 columns and 256 rows of light detectors, in which the rows are summed for each column to give a readout (output signal) indicative of the spectral content of the reflected light beam 15.

The readout (output signal) from the CCD detector array 5 is transmitted to a computer station 39 through an electric cable 27. This computer station 39 is responsive to the measured intensities of the components of different wavelengths of the light spectrum for computing and eventually displaying a graph of absorbance of the precise small area of the fundus of the patient's eye as a function of wavelength. As this graph of absorbance depends on and is directly related to the level of oxygenation of the precise small area of the fundus of the patient's eye, it can be easily converted by the computer station 39 to this oxygenation level. The computer station 39 will detect whether a change has occured in the oxygenation level in response to stimulation of the patient with the flickering stimulus. Such a change is indicative of neural integrity of the patient's central nervous system.

Figure 4:
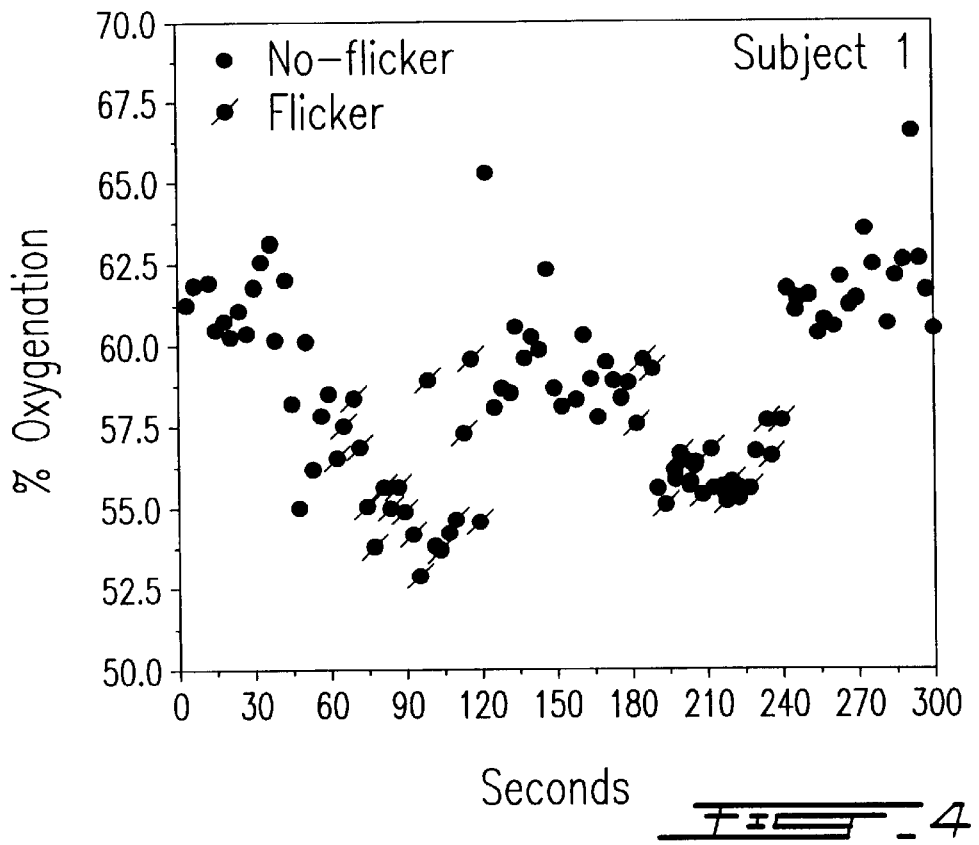
FIG. 4 is a graph showing individual data points of the level of oxygenation in the patient's second eye with respect to time (seconds) obtained from a human observer for a 5 minute testing sequence where the flickering light was alternately off for 60 seconds and on for 60 seconds.
Figure 5:
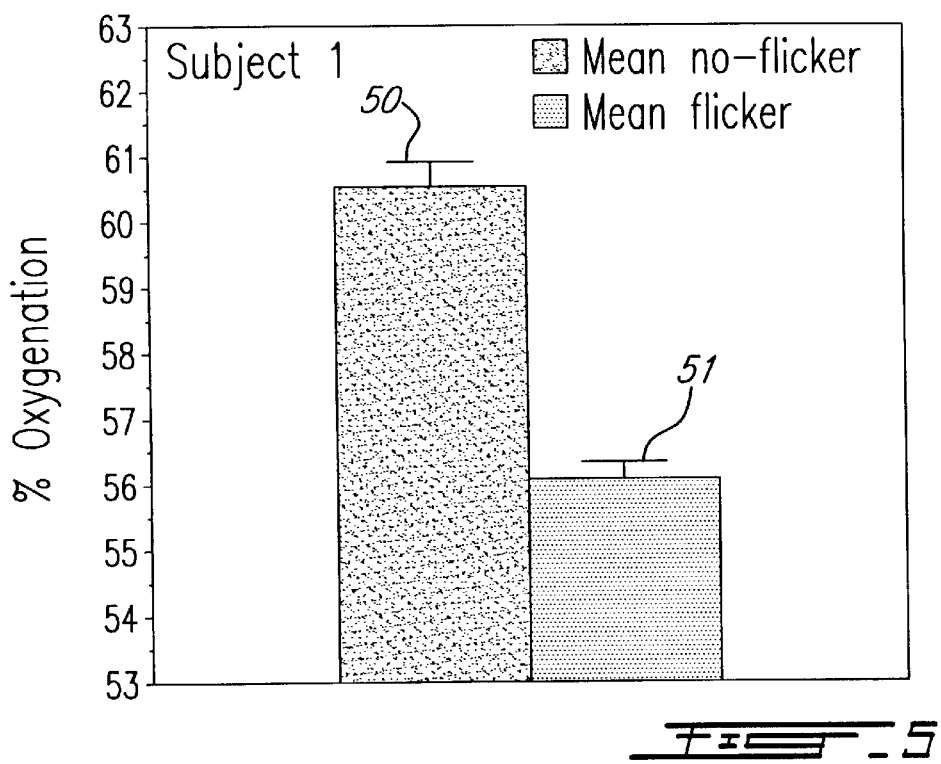
FIG. 5 is a graph showing the mean level of oxygenation in the patient's second eye for the non-flicker and flicker conditions along with the standard error bars.

Experiments have been conducted to demonstrate that detection of the interocular transfer effect of oxygenation is possible. An example of these data is illustrated in FIGS. 4 and 5. This example shows that the level of oxygenation measured at the optic nerve head of the second, recorded eye 103 (FIG. 1) can change by 4 to 5% while simply stimulating the first eye 101 with a 5 Hz flickering light 102. This is equivalent to the oxygenation changes produced in a given eye by reducing its ocular perfusion pressure between 15 to 30% which corresponds to a relatively large change (Faubert, J.; Gagnon, M.; Diaconu V.; (1999); "The O.S.O.M.E. System: A New Real-Time Non-Invasive Technique for Measuring Oxygenation and Hemoglobin in the Human Eye"; *Investigative Ophthalmology and Visual Science*, 40, S977).

FIG. 4 is a graph of the level of oxygenation of the patient's recorded eye 103 with respect to time. The graph of FIG. 4 shows individual data points obtained from a human observer for a 5 minute testing sequence where the flickering light was alternately off for 60 seconds and on for 60 seconds. The results show clear changes in oxygenation level as a consequence of the flicker-induced neural activity. This demonstrates the sensitivity of the technique.

FIG. 5 is a graph showing the mean oxygenation level of the patient's recorded eye 103 for the non-flicker and flicker conditions along with the standard error bars 50 and 51 indicating that the technique is not only sensitive but is quite reliable for measuring the interocular transfer.

Just a word to mention that similar results are obtained with an auditory flickering stimulus according to the embodiment of FIG. 2.

Although the present invention has been described hereinabove by way of a preferred embodiment thereof, this embodiment can be modified at will, within the scope of the appended claims, without departing from the spirit and nature of the subject invention.

What is claimed is:

1. A method for assessing neural integrity of a patient's central nervous system, comprising:
    stimulating the patient with a visual or auditory flickering stimulus;
    sensing oxygenation in at least one eye of the patient; and
    detecting whether a change in the sensed oxygenation occurs in response to stimulation of the patient with the flickering stimulus, said change being indicative of neural integrity of the patient's central nervous system.

2. An apparatus for assessing neural integrity of a patient's central nervous system, comprising:
    a generator of a visual or auditory flickering stimulus, said flickering stimulus being applied to the patient to stimulate said patient; and
    a neural integrity assessment instrument responsive to oxygenation in at least one eye of the patient, said neural integrity assessment instrument comprising:
        a sensor of oxygenation in at least one eye of the patient; and
        a detector of a change in the level of the sensed oxygenation in response to stimulation of said patient with the flickering stimulus, said change being indicative of neural integrity of the patient's central nervous system.

3. A method for assessing neural integrity of a patient's central nervous system, comprising:
    stimulating a first eye of the patient with a flickering light;
    sensing oxygenation in the patient's second eye; and
    detecting whether a change in the sensed oxygenation occurs in response to stimulation of the patient's first eye with flickering light, said change being indicative of neural integrity of the patient's central nervous system.

4. A method for assessing neural integrity of a patient's central nervous system as defined in claim 3, wherein sensing oxygenation in the patient's second eye comprises sensing levels of oxygenation at the optic nerve head of the fundus of the patient's second eye.

5. A method for assessing neural integrity of a patient's central nervous system as defined in claim 3, wherein stimulating the patient's first eye comprises adjusting at least one of the following parameters to generate at least one desired neural response of the patient's central nervous system: an intensity of the flickering light, a contrast of the flickering light, a color of the flickering light, a flicker rate of the flickering light, and a duration of the stimulation of the patient's first eye with flickering light.

6. An apparatus for assessing neural integrity of a patient's central nervous system, comprising:
   a generator of flickering light, said flickering light being applied to a first eye of the patient to stimulate said patient's first eye;
   a neural integrity assessment instrument responsive to oxygenation in the patient's second eye, said neural integrity assessment instrument comprising:
      a sensor of oxygenation in the patient's second eye; and
      a detector of a change in the level of the sensed oxygenation in response to stimulation of the patient's first eye with flickering light, said change being indicative of neural integrity of the patient's central nervous system.

7. An apparatus for assessing neural integrity of a patient's central nervous system as defined in claim 6, wherein said sensor is positioned to sense levels of oxygenation at the optic nerve head of the fundus of the patient's second eye.

8. An apparatus for assessing neural integrity of a patient's central nervous system as defined in claim 6, wherein said generator comprises a source of light operated through a flickering-light controller.

9. An apparatus for assessing neural integrity of a patient's central nervous system as defined in claim 8, wherein said source of light is selected from the group consisting of a light-emitting diode and a laser.

10. An apparatus for assessing neural integrity of a patient's central nervous system as defined in claim 8, further comprising a fiber optic cable interposed between the source of light and the patient's first eye, said fiber optic cable guiding light from the source of light to the patient's first eye.

11. An apparatus for assessing neural integrity of a patient's central nervous system as defined in claim 6, wherein the neural integrity assessment instrument comprises an on-line oxygenation measurement device.

12. A method for assessing neural integrity of a patient's central nervous system, comprising:
   stimulating at least one ear of the patient with an auditory flickering stimulus;
   sensing oxygenation in at least one eye of the patient; and
   detecting whether a change in the sensed oxygenation occurs in response to stimulation of said patient's at least one ear with the auditory flickering stimulus, said change being indicative of neural integrity of the patient's central nervous system.

13. A method for assessing neural integrity of a patient's central nervous system as defined in claim 12, wherein sensing oxygenation in said patient's at least one eye comprises sensing levels of oxygenation at the optic nerve head of the fundus of said patient's at least one eye.

14. A method for assessing neural integrity of a patient's central nervous system as defined in claim 12, wherein stimulating said patient's at least one ear comprises adjusting at least one of the following parameters to generate at least one desired neural response of the patient's central nervous system: an amplitude of the auditory flickering stimulus, a frequency of the auditory flickering stimulus, a pitch domain of the auditory flickering stimulus, a flicker rate of the auditory flickering stimulus, and a duration of the stimulation of the patient's at least one ear with the auditory flickering stimulus.

15. An apparatus for assessing neural integrity of a patient's central nervous system, comprising:
   a generator of an auditory flickering stimulus, said auditory flickering stimulus being applied to at least one ear of the patient to stimulate said patient's at least one ear;
   a neural integrity assessment instrument responsive to oxygenation in at least one eye of the patient, said neural integrity assessment instrument comprising:
      a sensor of oxygenation in said patient's at least one eye; and
      a detector of a change in the level of the sensed oxygenation in response to stimulation of said patient's at least one ear with the auditory flickering stimulus, said change being indicative of neural integrity of the patient's central nervous system.

16. An apparatus for assessing neural integrity of a patient's central nervous system as defined in claim 15, wherein said sensor is positioned to sense levels of oxygenation at the optic nerve head of the fundus of said patient's at least one eye.

17. An apparatus for assessing neural integrity of a patient's central nervous system as defined in claim 15, wherein said generator comprises a source of auditory flickering stimulus connected to an earphone.

18. An apparatus for assessing neural integrity of a patient's central nervous system as defined in claim 15, wherein the neural integrity assessment instrument comprises an on-line oxygenation measurement device.

* * * * *